United States Patent [19]

Grollier et al.

[11] Patent Number: 4,664,835
[45] Date of Patent: May 12, 1987

[54] WASHING AND FOAMING COMPOSITION BASED ON SURFACE-ACTIVE AGENTS AND ANIONIC POLYMERS

[75] Inventors: Jean F. Grollier, Paris; Claude Dubief, Le Chesnay, both of France

[73] Assignee: L'Oreal, Paris, France

[21] Appl. No.: 599,974

[22] Filed: Apr. 13, 1984

[30] Foreign Application Priority Data

Apr. 15, 1983 [LU] Luxembourg .................. 84.752

[51] Int. Cl.$^4$ .................. C11D 1/72; C11D 1/74; C11D 3/37
[52] U.S. Cl. .................. 252/90; 252/92; 252/542; 252/545; 252/548; 252/174.21; 252/174.22; 252/174.23; 252/174.24
[58] Field of Search .................. 252/174.21, 174.22, 252/174.23, 174.24, 545, 548, 542, DIG. 2, DIG. 3, DIG. 5, DIG. 13, DIG. 14, 90, 92; 424/70

[56] References Cited

U.S. PATENT DOCUMENTS

| | | | |
|---|---|---|---|
| 3,723,323 | 3/1973 | Morgan et al. | 252/90 |
| 3,836,637 | 9/1974 | Schmolka | 424/70 |
| 3,969,500 | 7/1976 | Kennerley | 424/10 |
| 4,128,631 | 12/1978 | Lundmark et al. | 424/70 |
| 4,154,706 | 5/1979 | Kenkare et al. | 252/547 |

FOREIGN PATENT DOCUMENTS

| | | |
|---|---|---|
| 0066342 | 12/1982 | European Pat. Off. . |
| 0089213 | 3/1984 | European Pat. Off. . |
| 2307775 | 10/1973 | Fed. Rep. of Germany . |
| 2277859 | 2/1976 | France . |
| 2380774 | 9/1978 | France . |
| 2403353 | 4/1979 | France . |
| 37908 | 4/1974 | Japan . |
| 957175 | 5/1964 | United Kingdom . |
| 2050165 | 1/1981 | United Kingdom . |
| 2050411 | 2/1981 | United Kingdom . |
| 2088209 | 6/1982 | United Kingdom . |
| 2098624A | 11/1982 | United Kingdom . |

*Primary Examiner*—Prince E. Willis
*Attorney, Agent, or Firm*—Fleit, Jacobson, Cohn & Price

[57] ABSTRACT

The invention relates to a washing and foaming composition containing, in a cosmetically acceptable medium, at least one surface-active agent having weak detergent properties which is polyoxyethyleneated fatty acid ester of sorbitol, a copolymer of ethylene oxide and propylene oxide, a carboxylic acid of a polyglycol ether, or an alkylpolypeptidate, and at least one anionic polymer, the weight ratio of the anionic polymer to the surface-active agent being greater than 0.1:1 expressed in terms of active ingredient.

27 Claims, No Drawings

WASHING AND FOAMING COMPOSITION BASED ON SURFACE-ACTIVE AGENTS AND ANIONIC POLYMERS

The present invention relates to washing and foaming compositions based on surface-active agents and anionic polymers, which are intended for washing keratin fibres, in particular human hair, and the skin.

For a long time, washing compositions containing surface-active agents and polymers have been known. Polymers serve to modify the properties of the fibres or skin or modify the rheology, the stability and the creamy appearance of the foams produced by such compositions.

Among surface-active agents, a number, especially non-ionic or weakly anionic surface-active agents, are known which have advantageous properties as regards tolerance by the skin, but which unfortunately, have insufficiently strong detergency properties, preventing them from being used effectively for washing the hair or skin.

Thus, even when provision was made to use such surface-active agents in compositions such as shampoos, in association with anionic, cationic or other polymers, it was found that the results in terms of washing were very inadequate because of the weak detergency properties of these compounds.

We have now discovered that, by using such surface-active agents, which are a priori weak detergents, in association with anionic polymers in certain proportions, the detergency of the compositions containing these surface-active agents can be considerably improved; it is this discovery which forms the subject of the present invention.

This result is particularly valuable for weakly detergent surface-active agents which are mild towards the skin. By virtue of this discovery, it is possible to prepare washing and foaming compositions, based on such surface-active agents, which have good detergency properties and are well tolerated by the skin.

The invention thus relates to washing and foaming compositions based on weakly detergent surface-active agents and at least one anionic polymer as well as to a process for washing or cleaning keratin fibres, in particular human hair, or the skin, using such compositions.

The washing and foaming composition of the present invention is essentially characterized in that it contains at least one weakly detergent surface-active agent chosen from polyoxyethyleneated fatty acid esters of sorbitol, copolymers of ethylene oxide and propylene oxide, carboxylic acids of polyglycol ethers, and alkyl-polypeptidates, and at least one anionic polymer.

The weight ratio of anionic polymer(s) to the surface-active agent(s) is greater than 0.1:1 and preferably 0.3:1 to 1.7:1, expressed in terms of weight of active ingredient.

The weakly detergent surface-active agents used in the compositions according to the invention are in themselves known and are essentially chosen with the aid of the following test.

10 drops of artificial sebum having the following composition:
Glycerol trioleate: 65 g
Squalene: 15 g
Oleic acid: 15 g
Cholesterol: 5 g
Cerol Black B: 0.07 g are poured into a 300 ml conical flask and distributed over the flask walls.

100 ml of water are then poured in, followed by 1 ml of a solution of the surface-active agent (10% active ingredient) in question. After mechanical shaking for 5 minutes, the quality of the emulsion obtained is assessed.

A score of 1 to 5 is awarded as follows:
1 = poor emulsion
2 = very moderate emulsion (very partial; the sebum is on the surface)
3 = moderate emulsion (partial; a few drops of sebum on the surface)
4 = very good emulsion (but non-uniform)
5 = total emulsion (total and fine).

Any surface-active agent having a score less than or equal to 3 in this test is considered as a "weakly detergent surface-active agent" as used herein.

The surface-active agents used in the compositions according to the invention are weak detergents and are mild towards the mucous membranes.

Among surface-active agents which are more particularly preferred according to the invention, there may be mentioned non-ionic surface-active agents chosen from:
polyoxyethyleneated fatty acid esters of sorbitol, such as $C_{12}$–$C_{18}$ acid esters of sorbitol polyoxyethyleneated with 15 to 20 mol of ethylene oxide, and more particularly sorbitan monolaurate, monopalmitate, monostearate or monooleate polyoxyethyleneated with 20 mol of ethylene oxide; and
copolymers of ethylene oxide and propylene oxide, preferably having a molecular weight of 1,000 to 20,000, such as the products sold under the name Pluronic F88, which has a molecular weight of 10,800, by Produits Chimiques Ugine Kuhlmann;
or weakly anionic surface-active agents such as:
carboxylic acids of polyglycol ethers, corresponding to the formula:

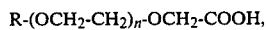

$$R\text{-}(OCH_2\text{-}CH_2)_n\text{-}OCH_2\text{-}COOH,$$

or salts thereof, in which the substituent R corresponds to a linear radical having from 6 to 18 carbon atoms and preferably 12 to 18 carbon atoms, and n is an integer from 5 to 25, preferably 5 to 10.

Among these products, there may be mentioned, more particularly, the product sold under the name Akypo RLM 100 by CHEM Y, corresponding to the above formula in which R denotes a mixture of alkyl radicals having 12 to 14 carbon atoms and n is equal to 10, and the product sold under the name Sandopan DTC acid by SANDOZ, corresponding to the above formula in which R denotes a group having 13 carbon atoms and n is equal to 7, and the salts of these compounds; and also Sandopan DTC linear gel and DTC linear acid, in which R denotes a mixture of radicals containing from 12 to 15 carbon atoms and n is equal to 5; Sandopan KST, in which R denotes an alkyl radical having 16 carbon atoms and n is equal to 12; and alkyl($C_8$–$C_{20}$)polypeptidates originating from the condensation of $C_8$–$C_{20}$ fatty acids and hydrolyzed proteins, such as the triethanolamine or potassium salts of the products of copra fatty acids and hydrolyzed animal proteins, sold under the names LAMEPON S by GRUNAU and MAYPON 4C or MAYPON 4 CT by STEPAN.

The anionic polymers used according to the invention are polymers generally having a molecular weight of 500 to 6,000,000 and preferably 5,000 to 1 million, and containing carboxylic or sulphonic acid groups.

The carboxylic acid groups are especially derived from unsaturated monocarboxylic or dicarboxylic acids represented by the formula:

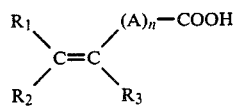

in which n is O or an integer from 1 to 10, A denotes a methylene group optionally joined to the carbon atom of the unsaturated group via a heteroatom such as oxygen or sulphur, or if n is greater than 1, the A groups can be optionally interrupted by a said heteroatom, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a group —$CH_2$—COOH or a phenyl or benzyl group.

In the above formula, the lower alkyl radicals preferably denote a group having from 1 to 4 carbon atoms, such as methyl or ethyl.

Among these polymers, those which are more particularly preferred are acrylic or methacrylic acid homopolymers or copolymers such as the products sold under the name GOODRITE K732 by GOODRITE, VERSICOL E or K by ALLIED COLLOIDS, and ULTRAHOLD 8 by CIBA-GEIGY, the sodium salts of acrylic acid/acrylamide copolymers sold under the name RETEN 421, 423 or 425 by HERCULES, the sodium polymethacrylate sold under the name DARVAN No. 7 by Van der BILT, the polyhydroxycarboxylic acid polymers sold under the name HYDAGEN F by HENKEL, and optionally monoesterified, unsaturated polymers containing an $\alpha$, $\beta$ dicarboxylic acid unit, such as the copolymers resulting from the copolymerization of a compound containing a group >C=$CH_2$ with a compound of the formula:

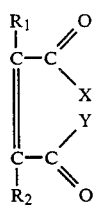

in which $R_1$ and $R_2$ independently of one another denote hydrogen, halogen or a sulphonic acid, alkyl, aryl or aralkyl group, X denotes OH and Y denotes OH, O-alkyl, O-aryl, NH-alkyl, NH-cycloalkyl or NH-aryl, or alternatively X and Y together denote O, i.e. an anhydride link is present.

There may be mentioned, in particular, unsaturated $\alpha$, $\beta$-dicarboxylic acids such as maleic, fumaric, itaconic, citraconic, phenylmaleic, benzylmaleic, dibenzylmaleic and ethylmaleic acids or the anhydrides of these acids, such as maleic anhydride, and also other derivatives such as the half-esters of these acids.

Examples which may be mentioned of compounds which can be polymerized and contain a group >C=$CH_2$ are vinyl esters, vinyl ethers, vinyl halides, phenylvinyl derivatives such as styrene, acrylic acid and its esters, and cinnamic acid esters. These polymers are described in greater detail in, for example, U.S. Pat. No. 2,047,398.

These polymers can optionally be esterified. More particularly valuable compounds are those described in U.S. Pat. Nos. 2,723,248 and 2,102,113 which have units of formula:

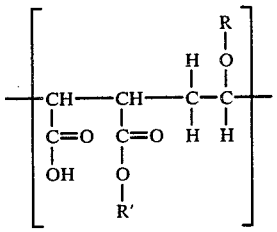

in which R represents an alkyl group having 1 to 4 carbon atoms, such as methyl, ethyl, propyl, isopropyl, butyl or isobutyl, and R' represents an alkyl group having 1 to 8 carbon atoms, such as methyl, ethyl, propyl, butyl, isobutyl, pentyl, hexyl, heptyl, octyl or isooctyl.

Other polymers of this type which can be used according to the invention are copolymers of maleic anhydride and an olefine having from 2 to 4 carbon atoms, which are partially esterified (e.g. 50 to 70%) by an alcohol having from 1 to 4 carbon atoms, these copolymers being described more particularly in British Pat. No. 839,805.

Other copolymers which can be used and which belong to this family are the copolymers resulting from the copolymerization of (a) an unsaturated acid anhydride such as maleic, citraconic or itaconic anhydride, and (b) an allyl or methallyl ester such as allyl or methallyl acetate, propionate, butyrate, hexanoate, octanoate, dodecanoate, octodecanoate, pivalate, neoheptanoate, neooctanoate, neodecanoate, 2-ethylhexanoate, 2,2,4,4-tetramethylvalerate or 2-isopropyl-2,3-dimethylbutyrate. The anhydride groups of these acids are either monoesterified with an aliphatic alcohol such as methanol, ethanol, propanol, isopropanol or n-butanol, or amidified with an aliphatic, cyclic or heterocyclic amine such as propylamine, isopropylamine, butylamine, dibutylamine, hexylamine, dodecylamine, morpholine, piperidine, pyrrolidine or N-methylpiperazine.

It is also possible to use the terpolymers resulting from the copolymerization of the monomers in paragraphs (a) and (b) above with an acrylamide or methacrylamide such as N-tert.-butylacrylamide, N-octylacrylamide, N-decylacrylamide, N-dodecylacrylamide, N-[(1,1-dimethyl)prop-1-yl]acrylamide, N-[(1,1-dimethyl)but-1-yl]acrylamide or N-[(1,1-dimethyl)pent-1-yl]acrylamide or the corresponding methacrylamides, the anhydride groups being esterified or amidified as indicated above.

The copolymers of this type can optionally also be copolymerized with $\alpha$-olefines such as prop-1-ene, but-1-ene, hex-1-ene, dodec-1-ene, hexadec-1-ene and octadec-1-ene, with vinyl ethers such as methyl vinyl ether, ethyl vinyl ether, propyl vinyl ether, isopropyl vinyl ether, butyl vinyl ether, hexyl vinyl ether, dodecyl vinyl ether, hexadecyl vinyl ether and octadecyl vinyl ether, with acrylic or methacrylic acid esters such as methyl, ethyl, propyl, isopropyl, butyl, tert.-butyl, hexyl, octyl, decyl, dodecyl, octadecyl, 2,3-dihydroxypropyl, $\omega$-methylpolyethylene glycol and $\omega$-ethylpolyethylene glycol acrylates and methacrylates, and, if appropriate, acrylic or methacrylic acid or N-vinylpyrrolidone in the case of the terpolymers. Polymers of this type are described in, e.g., French pat. application Nos. 2,350,834 and, 2,357,241.

Among the polymers belonging to this family, there may also be mentioned the polymers derived from maleic and itaconic acids and anhydrides mentioned above, and their copolymers with a monoethylenic unsaturated monomer such as ethylene, vinylbenzene, vinyl acetate, vinyl methyl ether or acrylamide, optionally hydrolyzed in the case of the anhydrides.

The polymers which are more particularly preferred are the products sold under the names Gantrez AN Nos. 119, 139, 149 and 169, which are maleic anhydride/-methyl vinyl ether copolymers (1:1), and Gantrez ES Nos. 225, 335, 425 and 435, which are respectively the monoethyl ester, monoisopropyl ester and monobutyl ester of poly(methyl vinyl ether/maleic anhydride), sold by General Aniline, EMA 91, which is the ethylene/maleic anhydride copolymer sold by the MONSANTO COMPANY, EMA 1325, which is the mono-n-butyl (poly)ethylene maleate sold by the MONSANTO COMPANY, and also the product sold under the name Gantrez S 95, which is the hydrolyzed form of poly(methyl vinyl ether/maleic anhydride).

It is also possible to use polyacrylamides containing carboxylate groups, sold especially by American Cyanamid under the name CYANAMER A 370.

Polymers containing sulphonic acid groups which can be used according to the invention are especially polyacrylamidesulphonic acid salts such as those mentioned in U.S. Pat. No. 4,128,631, and more particularly the polyacrylamidoethylpropanesulphonic acid sold under the name COSMEDIA POLYMER HSP 1180 by HENKEL.

These compositions should not contain cationic polymer, which would detract from the desired effect of the anionic polymer.

The total concentration of surface-active agent is suitably 0.5 to 20%, and preferably 3 to 10% by weight of active ingredient.

The total concentration of anionic polymer is suitably 0.05 to 15% and preferably 1 to 6% by weight of active ingredient.

The compositions generally have a pH of 2 to 10 and preferably 3 to 9. The pH can be adjusted with known alkalizing or acidifying agents.

These compositions can also contain anionic surface-active agents. It should be noted, however, that the improvement is detergency afforded by the association of an anionic polymer with a weakly detergent surface-active agent makes it possible to reduce the concentration of anionic surface-active agents which, in themselves, have good detergency properties.

These anionic surface-active agents are, in particular, alkali metal salts, ammonium salts, amine salts and aminoalcohol salts of the following compounds:
  alkyl-sulphates, alkyl-ether-sulphates, alkylamide-sulphatesand alkylamide-ether-sulphates, alkylarylpolyether-sulphates and monoglyceride-sulphates;
  alkylsulphonates, alkylamidesulphonates, alkylarylsulphonates, α-olefinesulphonates and paraffin-sulphonates;
  alkyl-sulphosuccinates, alkyl-ether-sulphosuccinates and alkylamide-sulphosuccinates;
  alkyl-sulphosuccinamates;
  alkyl-sulphoacetates and alkyl-polyglycerolcarboxylates;
  alkyl-phosphates and alkyl-ether-phosphates; and
  alkylsarcosinates, alkylisethionates and alkyltaurates, the alkyl radical in these various compounds being linear and having 12 to 18 carbon atoms; and
  fatty acids such as oleic acid, ricinoleic acid, palmitic acid, stearic acid and acids derived from copra oil or from hydrogenated copra oil. These anionic surface-active agents are suitably present in quantities not exceeding 8% of the total weight of the composition.

The compositions can take the normal forms used for compositions for washing the hair or skin and can be presented, in particular, in the form of aqueous or aqueous-alcoholic solutions which may or may not be thickened, creams, gels, dispersions, emulsions or aerosol foams. In addition to the weakly detergent surface-active agent or agents defined above and the anionic polymer or polymers, they can contain adjuvants normally used in cosmetics (with the exception of cationic polymer) such as perfumes, colourants, which can serve to colour either the composition itself or the hair or skin, preservatives, sequestering agents, thickeners, emulsifying agents, softeners, electrolytes, non-ionic polymers and, foam stabilizers, depending on the application envisaged.

These compositions can be used in the form of shampoos, bath foams, make-up remover compositions for the skin or eyes, and compositions for washing the skin.

The present invention also provides a process for washing and cleaning the skin or hair, which is essentially characterized in that at least one composition of this invention is applied to the hair or skin, and in that, if appropriate, after application, the hair or skin is rinsed with water by the traditional methods used in this field.

The Examples which follow further illustrate the present invention.

EXAMPLE 1

A shampoo having the following composition is prepared:

| | |
|---|---|
| Trideceth-7 carboxylic acid sold as a solution containing 90% of AI (Active Ingredient) under the name SANDOPAN DTC acid by SANDOZ | 5 g A.I. |
| Sodium salt of a polyhydroxycarboxylic acid, sold under the name HYDAGEN F by HENKEL | 5 g A.I. |
| Water, perfume, preservative q.s. pH = 7.4, adjusted with hydrochloric acid. | 100 g |

This composition has a greater detergency than that corresponding to 10% of surface-active agent in solution in water at a pH of 7.

When applied to dirty hair, it develops an unctuous and stable foam which is easy to rinse out. It washes the hair perfectly and, after rinsing, the wet hair is light.

The dried hair is bouncy, smooth and shiny.

EXAMPLE 2

A mild shampoo having the following composition is prepared:

| | |
|---|---|
| Sorbitan monlaurate polyoxyethyleneated with 20 mol of ethylene oxide, sold under | 5 g |

-continued

| | |
|---|---|
| the name TWEEN 20 by ATLAS | |
| Polyacrylic acid of MW $5.1.10^6$, sold at a concentration of 15% of active ingredient under the name VERSICOL E 17 by ALLIED COLLOIDS | 5 g AI |
| Water, perfume, preservative, colourant q.s. | 100 g |
| The pH is adjusted to 7 with sodium hydroxide. | |

The hair washed with this shampoo is light and bouncy.

Similar results are obtained on replacing the polymer with:

GOODRITE K 732 (acrylic polymer of MW 5000) or

COSMEDIA POLYMER HSP 1180.

EXAMPLE 3

A shampoo having the following composition is prepared:

| | |
|---|---|
| Sorbitan monolaurate polyoxyethyleneated with 20 mol of ethylene oxide, sold under the name TWEEN 20 by ATLAS | 5 g |
| Sodium and magnesium salts of sulphated lauryl alcohol oxyethyleneated with 4.5 mol of ethylene oxide | 3 g |
| Dodecanediol | 2 g |
| Vinyl methyl ether/maleic anhydride copolymer monoesterified with butanol, sold as a solution containing 50% of active ingredient in ethanol under the name GANTREZ ES 425 by General Aniline | |
| Sodium salt of polyacrylic acid, sold under the name HOES 2793 by HOECHST | 0.5 g |
| Water, perfume, preservative, colourant q.s. | 100 g |
| The pH is adjusted to 7 with sodium hydroxide. | |

EXAMPLE 4

A shampoo having the following composition is prepared:

| | |
|---|---|
| Sodium salt of trideceth-7 carboxylic acid of the formula: $CH_3(CH_2)_{11}CH_2(OCH_2CH_2)_7$—$OCH_2COONa$ sold under the name SANDOPAN DTC acid by SANDOZ | 5 g |
| Polyacrylic acid having a molecular weight of about 230,000, sold containing 25% of active ingredient under the name VERSICOL E11 by ALLIED COLLOIDS | 5 g AI |
| Water, perfume preservative, colourant q.s. | 100 g |
| The pH is adjusted to 7 with sodium hydroxide. | |

This composition has a greater detergency than that of the composition only comtaining 5% of SANDOPAN DTC acid.

EXAMPLE 5

The following composition is prepared:

| | |
|---|---|
| Potassium salt of the condensation product of coconut oil and collagen polypeptides, containing 30% of AI (active ingredient) sold under the name LAMEPON S by GRUNAU | 5 g AI |
| Polymethacrylic acid of approximate MW 26,000, containing 20% of AI, sold under the name VERSICOL K 13 by ALLIED COLLOIDS | 3 g AI |
| Water, perfume, preservative(s), colourant(s) q.s. | 100 g |

| | |
|---|---|
| pH = 6 with sodium hydroxide | |

This composition is used as a shampoo for washing the hair.

EXAMPLE 6

The following composition is prepared:

| | |
|---|---|
| Copolymer of ethylene oxide and propylene oxide, of MW 10,800, sold under the name PLURONIC F 88 by PCUK | 5 g |
| Polyacrylic acid of approximate MW 230,000, containing 25% of AI, sold under the name VERSICOL E 11 by ALLIED COLLOIDS | 5 g AI |
| Water, perfume, preservative(s), colourant(s) q.s. | 100 g |
| pH = 7 with sodium hydroxide | |

This composition is used as a shampoo for washing the hair.

EXAMPLE 7

The following composition is prepared:

| | |
|---|---|
| Trideceth-7 carboxylic acid of the formula: $CH_3$—$(CH_2)_{11}CH_2$—$(OCH_2$—$CH_2)_7OCH_2COOH$, containing 90% of AI, sold by SANDOZ under the name SANDOPAN DTC acid | 4 g AI |
| Polyacrylamidoethylpropanesulphonic acid sold containing 15% of AI under the name COSMEDIA POLYMER HSP 1180 by HENKEL | 5 g AI |
| Water, perfume, preservative, colourant q.s. | 100 g |
| pH = 6 with sodium hydroxide. | |

This composition is used as a shampoo for washing the hair.

EXAMPLE 8

The following composition is prepared:

| | |
|---|---|
| Potassium salt of the condensation product of coconut oil and collagen polypeptides, sold as a solution containing 30% of AI under the name LAMEPON S by GRUNAU | 5 g AI |
| Sodium salt of a polyhydroxycarboxylic acid, sold under the name HYDAGEN F by HENKEL | 5 g AI |
| Water, perfume, preservative q.s. | 100 g |
| pH = 7.0, adjusted with sodium hydroxide. | |

This composition is used as a shampoo for washing the hair.

EXAMPLE 9

The following composition is prepared:

| | |
|---|---|
| Sorbitan monolaurate polyoxyethyleneated with 20 mol of ethylene oxide, sold under the name TWEEN 20 by ATLAS | 6 g AI |
| Maleic anhydride/methyl vinyl ether copolymer sold under the name GANTREZ AN 119 by G.A.F. (in the form of the salt with NaOH) | 1 g AI |
| Water, perfume, preservative q.s. | 100 g |
| pH adjusted to 7 with hydrochloric acid. | |

This composition is used as a shampoo for washing the hair.

EXAMPLE 10

The following composition is prepared:

| | |
|---|---|
| Potassium salt of the condensation product of coconut oil and collagen polypeptides, containing 30% of AI, sold under the name LAMEPON S by GRUNAU | 10 g AI |
| Sodium polymethacrylate sold under the name DARVAN No. 7 by VAN DER BILT | 6 g AI |
| Water, perfume, preservative, colourant q.s. pH adjusted to 8 with sodium hydroxide. | 100 g |

This composition is used as a shampoo for washing the hair.

EXAMPLE 11

The following composition is prepared.

| | |
|---|---|
| Trideceth-7 carboxylic acid of the formula: $CH_3\text{-}(CH_2)_{11}CH_2\text{-}(OCH_2\text{-}CH_2)_7OCH_2COOH$, containing 90% of AI, sold under the name SANDOPAN DTC acid by SANDOZ | 1 g AI |
| Partially hydrolyzed polyacrylamide sold under the name CYANAMER A 370 by AMERICAN CYANAMID | 0.2 g AI |
| Water, perfume, preservative, colourant q.s. pH adjusted to 7 with sodium hydroxide. | 100 g |

This composition is a lotion for washing the hands and body.

EXAMPLE 12

The following composition is prepared:

| | |
|---|---|
| Copolymer of ethylene oxide and propylene oxide, of MW 10,800, sold under the name PLURONIC F88 by PCUK | 5 g AI |
| Polymethacrylic acid of approximate MW 10,000, containing 25% of AI, sold under the name VERSICOL K11 by ALLIED COLLOIDS | 3.2 g AI |
| Water, perfume, preservative q.s. pH = 7, adjusted with hydrochloric acid. | 100 g |

This composition is used as a shampoo for washing the hair.

EXAMPLE 13

The following composition is prepared:

| | |
|---|---|
| Copolymer of ethylene oxide and propylene oxide, of MW = 10,800, sold under the name PLURONIC F88 by PCUK | 5 g |
| Sodium polymethacrylate sold under the name DARVAN No. 7 by VAN DER BILT | 5 g |
| Water, perfume, preservative q.s. pH = 8, adjusted with hydrochloric acid. | 100 g |

This composition is used as a shampoo for washing the hair.

EXAMPLE 14

The following composition is prepared:

| | |
|---|---|
| Trideceth-7 carboxylic acid of the formula: $CH_3\text{---}(CH_2)_{11}\text{---}CH_2\text{---}(OCH_2\text{---}CH_2)_7OCH_2\text{---}COOH$, containing 90% of AI, sold under the name SANDOPAN DTC acid by SANDOZ | 6 g AI |
| Potassium salt of the condensation product of coconut oil and collagen polypeptides, containing 30% of AI, sold under the name LAMEPON S by GRUNAU | 6 g AI |
| Sodium salt of polyhydroxycarboxylic acid, sold under the name HYDAGEN F by HENKEL | 6 g AI |
| Water, perfume, preservative q.s. pH = 6.7, adjusted with sodium hydroxide. | 100 g |

This composition is used to prepare bath foams.

EXAMPLE 15

The following composition is prepared:

| | |
|---|---|
| Carboxylic acid of polyglycol ether, of the formula: $R\text{---}(O\text{---}CH_2\text{---}CH_2)_x\text{---}OCH_2\text{---}COOH$ in which $R = C_{12}\text{-}C_{14}$ and $x = 10$, sold containing 90% of AI under the name AKYPO RLM 100 by CHEM Y | 0.7 g AI |
| Hydrolyzed methyl vinyl ether/maleic anhydride copolymer sold under the name GANTREZ S 95 by GAF | 1 g AI |
| Water, perfume, preservative q.s. pH = 4.5, adjusted with hydrochloric acid. | 100 g |

This composition is used as a make-up remover for the eyes.

EXAMPLE 16

The following composition is prepared:

| | |
|---|---|
| Sorbitan monolaurate polyoxyethyleneated with 20 mol of ethylene oxide, sold under the name TWEEN 20 by ATLAS | 5 g AI |
| Partially hydrolyzed polyacrylamide sold under the name CYANAMER A 370 by AMERICAN CYANAMID | 5 g AI |
| Water, perfume, colourant q.s. | 100 g |

This composition is used as a shampoo for washing the hair.

We claim:

1. A washing and foaming composition which comprises, in a cosmetically acceptable medium,
    (i) about 3 to about 10% by weight of a surface-active agent having weak detergent properties selected from the group consisting of polyoxyethyleneated fatty acid esters of sorbitol, copolymers of ethylene oxide and propylene oxide, and alkylpolypeptidates; and
    (ii) about 1 to about 6% by weight of an anionic polymer having a molecular weight of 500 to 6,000,000 and containing carboxylic or sulphonic acid groups, different from a crosslinked acrylic acid homopolymer; the weight ratio of the anionic polymer to the surface-active agent being between about 0.3 and about 1.7 expressed in terms of weight of active ingredient, said washing and foaming composition containing no polymers which carry a cationic group.

2. A composition according to claim 1 in which the surface-active agent is selected from the group consisting of $C_{12}\text{-}C_{18}$ acid esters of sorbitol polyoxyethyleneated with 15 to 20 mol of ethylene oxide, copolymers of ethylene oxide and propylene oxide having a molecular weight of 1,000 to 20,000, and alkyl($C_8\text{-}C_{20}$)polypeptidates.

3. A composition on according to claim 1 in which the anionic polymer is a polymer derived from unsaturated monocarboxylic or dicarboxylic acids selected from the group consisting of:
a product of the formula:

$$\begin{array}{c} R_1 \\ \phantom{R}\diagdown \\ \phantom{RR}C=C \\ \phantom{R}\diagup \\ R_2 \end{array}\begin{array}{c} (A)_n\text{—COOH} \\ \diagup \\ \phantom{R} \\ \diagdown \\ R_3 \end{array}$$

in which
n is 0 or an integer from 1 to 10,
A denotes a methylene group,
$R_1$ denotes a hydrogen atom or a phenyl or benzyl group,
$R_2$ denotes a hydrogen atom or a lower alkyl or carboxyl group, and
$R_3$ denotes a hydrogen atom, a lower alkyl group, a —CH$_2$—COOH group, or a phenyl or benzyl group;
a product of the formula:

$$\begin{array}{c} R_1 \\ \phantom{R}\diagdown \\ \phantom{RR}C=C \\ \phantom{R}\diagup \\ R_2 \end{array}\begin{array}{c} (A)_n\text{—COOH} \\ \diagup \\ \phantom{R} \\ \diagdown \\ R_3 \end{array}$$

in which
n is 0 or an integer from 1 to 10,
A denotes a methylene group which is joined to the carbon atom of the unsaturated group via a heteroatom, said heteroatom being an oxygen or a sulful atom,
$R_1$ denotes a hydrogen atom or a phenyl or benzyl group,
$R_2$ denotes a hydrogen atom or a lower alkyl or carboxyl group, and
$R_3$ denotes a hydrogen atom, a lower alkyl group, a —CH$_2$—COOH group or a phenyl or benzyl group;
a product of the formula:

$$\begin{array}{c} R_1 \\ \phantom{R}\diagdown \\ \phantom{RR}C=C \\ \phantom{R}\diagup \\ R_2 \end{array}\begin{array}{c} (A)_n\text{—COOH} \\ \diagup \\ \phantom{R} \\ \diagdown \\ R_3 \end{array}$$

in which
n is an integer from 2 to 10,
A denotes a methylene group, said A groups being connected via a heteroatom which is an oxygen or a sulfur atom,
$R_1$ denotes a hydrogen atom or a phenyl or benzyl group,
$R_2$ denotes a hydrogen atom or a lower alkyl or carboxy group, and
$R_3$ denotes a hydrogen atom, a lower alkyl group, a —CH$_2$—COOH group or a phenyl or benzyl group; and
a product of the formula:

$$\begin{array}{c} R_1 \\ \phantom{R}\diagdown \\ \phantom{RR}C=C \\ \phantom{R}\diagup \\ R_2 \end{array}\begin{array}{c} (A)_n\text{—COOH} \\ \diagup \\ \phantom{R} \\ \diagdown \\ R_3 \end{array}$$

in which n is an integer from 2 to 10,
A denotes a methylene group which is joined to the carbon atom of the unsaturated group via a heteroatom which is an oxygen or a sulfur atom, said A groups being connected via a heteroatom which is an oxygen or a sulfur atom,
$R_1$ denotes a hydrogen atom or a phenyl or benzyl group,
$R_2$ denotes a hydrogen atom or a lower alkyl or carboxyl group, and
$R_3$ denotes a hydrogen atom, a lower alkyl group, a —CH$_2$—COOH group or a phenyl or benzyl group different from a crosslinked acrylic acid homopolymer.

4. A composition according to claim 3, in which the anionic polymer is selected from the group consisting of a crosslinked acrylic and methacrylic acid homopolymers and copolymers, acrylamide-carboxylic acid copolymers, polyhydroxycarboxylic acid polymers, polymers derived from maleic, fumaric, itaconic, citraconic, phenylmaleic, dibenzylmaleic or ethylmaleic acids, polymers derived from anhydrides of said acids, and polymers derived from half-esters of said acids.

5. A composition according to claim 4 wherein said anionic polymer is copolymerized with a compound containing a >C=CH$_2$ group selected from the group consisting of ethylene, vinyl, allyl and methallyl esters, vinyl ethers, vinyl halides, phenylvinyl derivatives, acrylic or methacrylic acids and esters thereof, substituted and unsubstituted acrylamides and methacrylamides, α-olefines, N-vinylpyrrolidones and cinnamic acid esters.

6. A composition according to claim 1, in which the anionic polymer is a polyacrylamide-sulfonic acid salt.

7. A composition according to claim 1, which has a pH of 2 to 10.

8. A composition according to claim 1, which also contains an anionic surface-active agent.

9. A composition according to claim 8, in which the anionic surface-active agent is present in an amount not exceeding 8% by weight.

10. The washing and foaming composition for hair and skin of claim 1 wherein
the surface active agent is polyoxyethyleneated fatty acid ester of sorbitol; and
the anionic polymer is selected from the group consisting of a non crosslinked homopolymer of acrylic acid, a copolymer of acrylic acid, a homo or copolymer of methacrylic acid, a carboxylic polyacrylamide, a maleic anhydride/methyl vinylether copolymer, a polyhydroxycarboxylic acid polymer and a polyacrylamidoethyl propane sulphonic acid polymer.

11. The washing and foaming composition for hair and skin of claim 1 wherein
the surface active agent is a copolymer of ethylene oxide and propylene oxide and is present in an amount of 3 to 10%; and
the anionic polymer is selected from the group consisting of a non crosslinked homopolymer of acrylic acid, a copolymer of acrylic acid, a homo or copolymer of methacrylic acid, a carboxylic polyacrylamide, a polyhydroxycarboxylic acid polymer, and a polyacrylamidoethyl propane sulphonic acid polymer.

12. The washing and foaming composition for hair and skin of claim 1 wherein
the surface active agent is an alkyl polypeptidate; and the anionic polymer is selected from the group consisting of a non crosslinked homopolymer of acrylic acid, a copolymer of acrylic acid, a homo or copolymer of methacrylic acid, a carboxylic polyacrylamide, a maleic anhydride/methyl vinylether copolymer, a polyhydroxycarboxylic acid polymer, and a polyacrylamidoethyl propane sulphonic acid polymer.

13. A composition according to claim 1, which is in a form selected from the group consisting of: an aqueous or aqueous-alcoholic solution, a thickened aqueous or aqueous-alcoholic solution, a cream, a gel, a dispersion, an emulsion and an aerosol foam.

14. A process for washing or cleaning keratin fibres or the skin, which comprises applying thereto at least one composition as claimed in claim 1.

15. A washing and foaming composition for hair and skin consisting essentially of:
(i) a surface active agent having weak detergent properties which is a carboxylic acid of a polyglycolether of the formula:

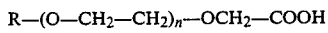

R—(O—CH$_2$—CH$_2$)$_n$—OCH$_2$—COOH and salts thereof, wherein R is a linear (C$_6$–C$_{18}$) alkyl, and n is an integer from 5 to 25;
(ii) at least one anionic polymer having a molecular weight of between 500 and 6,000,000 and sulphonic acid groups or carboxylic acid groups selected from the group consisting of acrylamide-carboxylic acid copolymers, polyhydroxycarboxylic acid polymers, polymers derived from maleic, fumaric, itaconic, citraconic, phenylmaleic, dibenzylmaleic or ethylmaleic acids, polymers derived from anhydrides of said acids, polymers derived from half-esters of said acids, and copolymers of said acids copolymerized with a compound containing a >C=CH$_2$ group selected from the group consisting of ethylene, vinyl halides, phenylvinyl derivatives, acrylic or methacrylic acids and esters thereof, substituted and unsubstituted acrylamides and methacrylamide, α-olefines, N-vinyl pyrrolidones and cinnamic acid esters; the weight ratio of the anionic polymer to the surface active agent being greater than 0.1:1 expressed in terms of weight of active ingredient, and a cosmetically acceptable adjuvant being other than a polymer carrying cationic groups.

16. The composition according to claim 15 wherein the anionic polymer is a sulphonic acid polymer which is a polyacrylamid sulphonic salt or a carboxylic acid polymer selected from the group consisting of polyhydroxycarboxylic acids, polyacrylamide carboxylates, copolymers of maleic anhydrid/methylvinyl ether and their hydrolyzed forms, monomethyl esters, monoisoprophylesters or monobutylesters of poly(methylvinylether/maleic anhydride), poly(ethylene/mono n-butyl maleate), and copolymers of ethylene/maleic anhydrid.

17. The composition of claim 15 further comprising an anionic surface active agent in an amount not exceeding 8% by weight.

18. The composition of claim 15 wherein
the anionic polymer is present in an amount of between 0.05 to 15% by weight; and
the non-ionic surface active agent is present in an amount of between 0.5 to 20% by weight.

19. A process for washing and cleaning hair and skin comprising applying the composition of claim 15 to said hair and skin, in an amount effective to attain said effect.

20. A process for washing and cleaning hair and skin comprising applying thereto a composition comprising, in a cosmetically acceptable medium,
(i) at least one surface-active agent having weak detergent properties selected from the group consisting of polyoxyethyleneated fatty acid esters of sorbitol, copolymers of ethylene oxide and propylene oxide, and alkylpolypeptidates; and
(ii) at least one anionic polymer having a molecular weight of 500 to 6,000,000 and containing carboxylic or sulphonic acid groups, different from a crosslinked of acrylic acid homopolymer; the weight ratio of the anionic polymer to the surface-active agent being between about 0.3 and about 1.7 expressed in terms of weight of active ingredient; said washing and foaming composition containing no polymers which carry a cationic group.

21. The process of claim 20 wherein the surface-active agent is selected from the group consisting of (C$_{12}$–C$_{18}$)acid esters of sorbitol polyoxyethyleneated with 15 to 20 mol of ethylene oxide, copolymers of ethylene oxide and propylene oxide having a molecular weight of 1,000 to 20,000, and alkyl(C$_8$–C$_{20}$)polypeptidates.

22. The process of claim 20 wherein the anionic polymer is a polymer derived from an unsaturated monocarboxylic or dicarboxylic acid selected from the group consisting of:
a product of the formula:

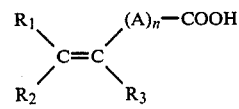

wherein
n is 0 or an integer from 1 to 10,
A denotes methylene,
R$_1$ denotes hydrogen, phenyl or benzyl,
R$_2$ denotes hydrogen, lower alkyl or carboxyl, and
R$_3$ denotes hydrogen, lower alkyl, —CH$_2$—COOH, phenyl or benzyl;
a product of the formula:

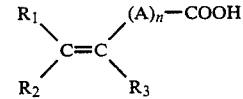

in which
n is 0 or an integer from 1 to 10,
A denotes a methylene group which is joined to the carbon atom of the unsaturated group via a heteroatom, said heteroatom being an oxygen or a sulfur atom,
R$_1$ denotes hydrogen, phenyl or benzyl,
R$_2$ denotes hydrogen, lower alkyl or carboxyl, and
R$_3$ denotes hydrogen, lower alkyl, —CH$_2$—COOH, phenyl or benzyl;
a product of the formula:

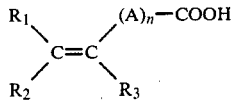

in which
- n is an integer from 2 to 10,
- A denotes a methylene group, said A groups being connected via a heteroatom which is an oxygen or a sulfur atom, $R_1$ denotes hydrogen, phenyl or benzyl,
- $R_2$ denotes hydrogen, lower alkyl or carboxyl, and
- $R_3$ denotes hydrogen, lower alkyl, —$CH_2$—COOH, pheyl or benzyl; and a product of the formula:

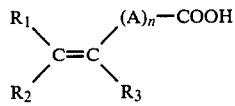

in which
- n is an integer from 2 to 10,
- A denotes a methylene group which is joined to the carbon atom of the unsaturated group via a heteroatom which is an oxygen or a sulfur atom, said A groups being connected via a heteroatom which is an oxygen or a sulfur atom,
- $R_1$ denotes hydrogen, phenyl or benzyl,
- $R_2$ denotes hydrogen, lower alkyl or carboxyl, and
- $R_3$ denotes hydrogen, lower alkyl, —$CH_2$—COOH, phenyl or benzyl, different from a crosslinked arcylic acid homopolymer.

23. The process of claim 22 wherein the anionic polymer is selected from the group consisting of non-crosslinked acrylic and methacrylic acid homopolymers and copolymers, acrylamide-carboxylic acid copolymers, polyhydroxycarboxylic acid polymers, polymers derived from maleic, fumaric, itaconic, citraconic, phenylmaleic, dibenzylmaleic or ethylmaleic acids, polymers derived from anydrides of said acids, and polymers derived from half-esters of said acids.

24. The process of claim 20 wherein the applied composition is in a form selected from the group consisting of:
- an aqueous or aqueous-alcoholic solution,
- a thickened aqueous or aqueous-alcoholic solution,
- a cream,
- a gel,
- a dispersion,
- an emulsion, and
- an aerosol foam.

25. The process of claim 23 wherein said anionic polymer is copolymerized with a compound containing a >C=$CH_2$ group selected from the group consisting of ethylene, vinyl, allyl and methallyl esters, vinyl ethers, vinyl halides, phenylvinyl derivatives, acrylic or methacrylic acids and esters thereof, substituted and unsubstituted acrylamides and methacrylamides, α-olefines, N-vinylpyrrolidones and cinnamic acid esters.

26. The process of claim 20 wherein the anionic polymer is a polyacrylamide-sulfonic acid salt.

27. The process of claim 20 wherein
- the surface-active agent is present in an amount from 0.5 to 20% by weight, and
- the anionic polymer is present in an amount from 0.05 to 15% expressed by weight of active ingredient.

* * * * *